United States Patent
Kuo (10) Patent No.: US 12,097,013 B2
(45) Date of Patent: Sep. 24, 2024

(54) DEVICE AND METHOD FOR PULSE DIAGNOSIS MEASUREMENT

(71) Applicant: Contemporary Han Cloud Co., Ltd, Taipei (TW)

(72) Inventor: Yu-Cheng Kuo, Taipei (TW)

(73) Assignee: Contemporary Han Cloud Co., Ltd, Taipei (TW)

( * ) Notice: Subject to any disclaimer, the term of this patent is extended or adjusted under 35 U.S.C. 154(b) by 299 days.

(21) Appl. No.: 16/435,578

(22) Filed: Jun. 10, 2019

(65) Prior Publication Data

US 2019/0374112 A1 Dec. 12, 2019

Related U.S. Application Data (60) Provisional application No. 62/683,626, filed on Jun. 11, 2018.

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02108* (2013.01); *A61B 5/026* (2013.01);
(Continued)

(58) Field of Classification Search
CPC ..... A61B 5/4854; A61B 7/045; A61B 17/135; A61B 17/1355; A61B 17/132; A61H 2230/30
See application file for complete search history.

(56) References Cited

U.S. PATENT DOCUMENTS 5,335,665 A 8/1994 Suzuki
5,730,138 A 3/1998 Wang
(Continued)

FOREIGN PATENT DOCUMENTS

CN 106540374 A 3/2017
JP 61-199835 A 9/1986
(Continued)

OTHER PUBLICATIONS

"Liu, Shing-Hong; Wang, Jia-Jung; Huang, Kuo-Sheng. A New Oscillometry-Based Method for Estimating the Brachial Arterial Compliance Under Loaded Conditions. Oct. 3, 2008. IEEE Transactions on Biomedical Engineering. vol. 55, Issue: 10. pp. 2463-2470" (Year: 2008).*
(Continued)

*Primary Examiner* — Benjamin S Melhus
*Assistant Examiner* — Severo Antonio P Lopez
(74) *Attorney, Agent, or Firm* — Winston Hsu (57) ABSTRACT

A pulse diagnosis measurement device comprises a sensing device, for sensing a blood pressure wave of an organism, to generate a pulse signal; a pulse-holding device, for applying a pressure on a pulse of the organism, wherein the pulse-holding device has an elasticity coefficient, the elasticity coefficient is corresponding to a frequency of a harmonic of the blood pressure wave, and the harmonic is an integer harmonic or a fractional harmonic; and a processing device, for generating pulse diagnosis information of the harmonic according to the pulse signal.

8 Claims, 8 Drawing Sheets

(51) Int. Cl.
  *A61B 5/021*  (2006.01)
  *A61B 5/026*  (2006.01)
(52) U.S. Cl.
  CPC .......... *A61B 5/6831* (2013.01); *A61B 5/7257* (2013.01); *A61B 5/6826* (2013.01); *A61B 5/7264* (2013.01)

(56) References Cited

U.S. PATENT DOCUMENTS

| | | | |
|---|---|---|---|
| 2009/0209868 A1* | 8/2009 | Hersh | A61B 5/02225 600/485 |
| 2010/0298726 A1 | 11/2010 | Kim | |
| 2017/0071823 A1 | 3/2017 | Chao | |
| 2017/0181649 A1* | 6/2017 | Carter | A61B 5/02416 |
| 2017/0215749 A1* | 8/2017 | Zhuo | A61B 5/02055 |
| 2017/0258336 A1* | 9/2017 | Furness, III | A61B 5/026 |
| 2018/0318593 A1* | 11/2018 | Sullivan | A61B 5/7203 |
| 2019/0111298 A1* | 4/2019 | Whalen | A61H 9/0092 |

FOREIGN PATENT DOCUMENTS

| | | |
|---|---|---|
| JP | 2-46824 A | 2/1990 |
| JP | 7-95966 A | 4/1995 |
| JP | 2012-29967 A | 2/2012 |
| JP | 2018-42606 A | 3/2018 |
| KR | 10-2012-0021098 A | 3/2012 |
| WO | 2007/067690 A2 | 6/2007 |
| WO | 2007/067690 A3 | 6/2007 |
| WO | 2012/004559 A1 | 1/2012 |
| WO | 2018/054665 A1 | 3/2018 |

OTHER PUBLICATIONS

Alex Yartsev, Resonance, damping and frequency response, Deranged Physiology, CICM Primary Exam, Required Reading, Cardiovascular system, Jan. 20, 2018, pp. 1-12, XP055632271.

William Craelius et al, Rhythm Analysis of Arterial Blood Pressure, IEEE Transactions on Biomedical Engineering , No. 12, Dec. 1986, p. 1166-1172, vol. BME-33, IEEE, XP011173883 , Dec. 1986.

* cited by examiner

FIG. 1

| | N-th harmonic | | 1/2$^m$-th harmonic |
|---|---|---|---|
| n = 1 | Jueyin Liver Channel of Foot | m = 1 | Jueyin Pericardium Channel of Hand |
| n = 2 | Shaoyin Kidney Channel of Foot | m = 2 | Shaoyin Heart Channel of Hand |
| n = 3 | Taiyin Spleen Channel of Foot | m = 3 | Yang linking vessel |
| n = 4 | Taiyin Lung Channel of Hand | m = 4 | Yin linking vessel |
| n = 5 | Yangming Stomach Channel of Foot | m = 5 | Yang Heel Vessel |
| n = 6 | Shaoyang Gallbladder Channel of Foot | m = 6 | Yin Heel Vessel |
| n = 7 | Taiyang Bladder Channel of Foot | m = 7 | Girdle Vessel |
| n = 8 | Yangming Large Intestine Channel of Hand | m = 8 | Governing Vessel |
| n = 9 | Shaoyang Sanjiao Channel of Hand | m = 9 | Directing Vessel |
| n = 10 | Taiyang Small Intestine Channel of Hand | m = 10 | Penetrating Vessel |

FIG. 2

| Harmonic | Pressure-strain modulus |
|---|---|
| $1/2^{10} \sim 1/2^8$ | $0.16*10^6 \sim 0.76*10^6$ |
| $1/2^7 \sim 1/2^4$ | $0.76*10^6 \sim 1.26*10^6$ |
| $1/2^3 \sim 1$ | $1.26*10^6 \sim 4.22*10^6$ |
| $1 \sim 4$ | $4.22*10^6 \sim 5.77*10^6$ |
| $5 \sim 9$ | $5.77*10^6 \sim 9.82*10^6$ |
| 10 and its above | Above $9.82*10$ |

FIG. 3

| Harmonic | Pressure-strain modulus |
|---|---|
| $1/2^{10} \sim 1/2$ | $0.16*10^6 \sim 3.5*10^6$ |
| $1 \sim 10$(or above 10) | $3.5*10^6 \sim 9.82*10^6$(or above $9.82*10^6$) |

| | | |
|---|---|---|
| n = 1 | T > 6 seconds | |
| n = 2 | T > 6 seconds | |
| n = 3 | T > 7 seconds | |
| n = 4 | T > 14 seconds | |
| n = 5 | T > 28 seconds | |
| n = 6 | T > 56 seconds | |
| n = 7 | T > 1.875 minutes | |
| n = 8 | T > 3.75 minutes | |
| n = 9 | T > 7.5 minutes | |
| n = 10 | T > 15 minutes | |

DEVICE AND METHOD FOR PULSE DIAGNOSIS MEASUREMENT

CROSS REFERENCE TO RELATED APPLICATIONS

This application claims the benefit of U.S. Provisional Application No. 62/683,626 filed on Jun. 11, 2018, which is incorporated herein by reference.

BACKGROUND OF THE INVENTION

1. Field of the Invention

The present invention relates to a pulse diagnosis of an organism, and more particularly, to a device and a method for a pulse diagnosis measurement.

2. Description of the Prior Art

When a pulse diagnosis device or an electronic blood pressure monitor is used for measuring a blood pressure wave of an organism (e.g., a human or another animal) or for performing a pulse diagnosis, a tourniquet is touched to a position of a pulse for performing the measurement to understand a physiological condition of the organism. However, accuracy of the measurement is affected by the tourniquet, especially when it is needed to measure harmonics of the blood pressure wave with high accuracy. Quality of the tourniquet has a major impact. Thus, design of a proper tourniquet is an important problem to be solved.

In the prior art, a pressure of the tourniquet is increased until the pressure is greater than a systolic blood pressure to block a blood flow of an arterial, and the pressure of the tourniquet is decreased until a Korotkoff sound (e.g., corresponding samples of the Korotkoff sound in an electronic blood pressure monitor) exists, such that the systolic blood pressure and a diastolic blood pressure can be obtained. Not only more time is needed for completing the measurement, but also the accuracy of the measurement is reduced due to that the blood flow of the arterial is blocked and the arterial is affected. Thus, performing a proper pulse diagnosis is also an important problem to be solved.

SUMMARY OF THE INVENTION

The present invention therefore provides a device and a method for a pulse diagnosis measurement to improve a pulse diagnosis of an organism to solve the abovementioned problem.

A pulse diagnosis measurement device comprises a sensing device, for sensing a blood pressure wave of an organism, to generate a pulse signal; a pulse-holding device, for applying a pressure on a pulse of the organism, wherein the pulse-holding device has a first elasticity coefficient, the first elasticity coefficient is corresponding to a first frequency of a first harmonic of the blood pressure wave, and the first harmonic is a first integer harmonic or a first fractional harmonic; and a processing device, for generating pulse diagnosis information of the first harmonic according to the pulse signal.

A method of pulse diagnosis measurement comprises applying a pressure to a pulse of an organism via a pulse-holding device; sensing a blood pressure wave of the organism via a sensing device, to generate a first pulse signal; computing a pulse pressure according to the first pulse signal; continuing adjusting the pressure of the pulse-holding device until the pulse pressure is not increased, at which time the pressure has a most suitable pressure value; and sensing the blood pressure wave according to the most suitable pressure value, to generate a second pulse signal.

A pulse diagnosis measurement device comprises a sensing device, for sensing a blood pressure wave of an organism, to generate a first pulse signal; a pulse-holding device, for applying a pressure to a pulse of the organism; and a processing device, for calculating a pulse pressure according to the first pulse signal, for continuing adjusting the pressure of the pulse-holding device until the pulse pressure is not increased, at which time the pressure has a most suitable pressure value, and for sensing the blood pressure wave according to the most suitable pressure value, to generate a second pulse signal.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
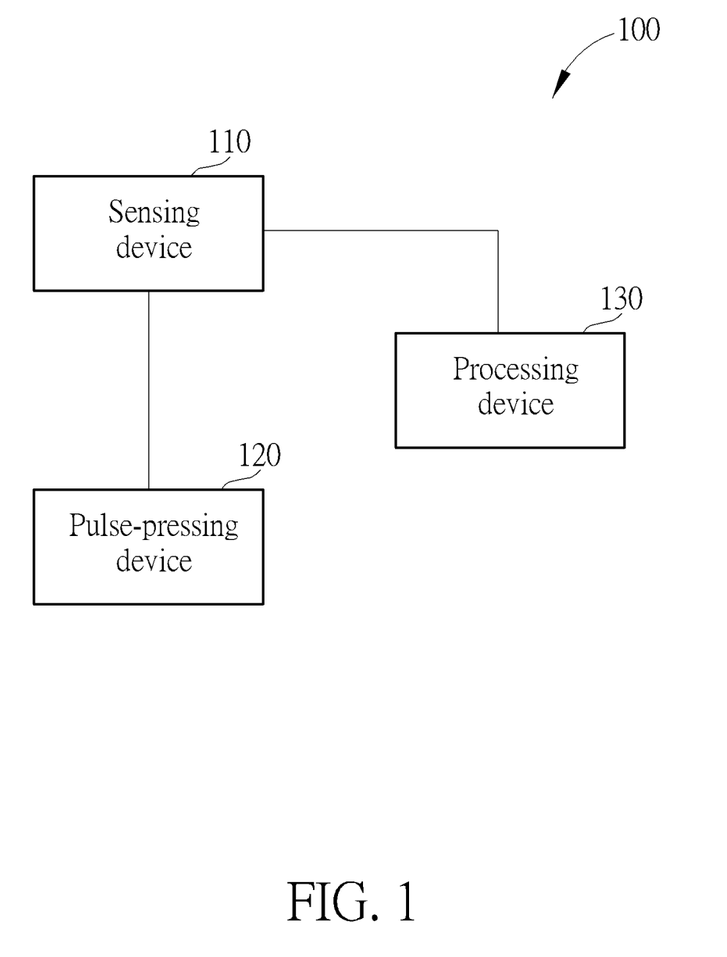
FIG. 1 is a schematic diagram of a pulse diagnosis measurement device according to an example of the present invention.

FIG. 1 is a schematic diagram of a pulse diagnosis measurement device according to an example of the present invention. In FIG. 1, a pulse diagnosis measurement device 100 may be a pulse diagnosis device, an electronic blood pressure monitor, a finger diagnosis device or other blood pressure wave measurement device. As shown in FIG. 1, the pulse diagnosis measurement device 100 includes a sensing device 110, for sensing a blood pressure wave of an organism (e.g., a human or another animal), to generate a pulse signal. The pulse diagnosis measurement device 100 further includes a pulse-holding device 120, for applying a pressure on a pulse of the organism, to facilitate the sensing device 110 to sense the blood pressure wave. For example, the pulse-holding device 120 may be a tourniquet. When a position of the pulse is a wrist, an arm, a finger or a neck, the tourniquet can enclose the pulse to apply a pressure. For example, the pulse-holding device 120 may be designed as a clip for performing a measurement by clamping the pulse, e.g., a finger diagnosis device, which can perform the measurement by clamping a finger tip. For example, the pulse-holding device 120 may include an elastic material such as elastic cloth and is made as an elastic wearable device, e.g., a finger cot, a watch, a bracelet, a wristband, an armband, an ankle ring, a headscarf or a collar, to sense the pulse at different parts of a body. In one example, the sensing device 110 is a pressure sensor such as a piezoelectric element, to sense a pressure, and the sensed pressure can be converted into an electronic signal. The sensing device 110 can contact the position of the pulse, and the pulse-holding device 120 applies a pressure on a top of the sensing device 110, such that the sensing device 110 can accurately sense beats of the pulse. In another example, the sensing device 110 is a pressure sensor and the pulse-holding device 120 is an inflatable cuff or bag. The sensing device 110 may be inflated or deflated to adjust a pressure on the pulse. The sensing device 110 is coupled to the pulse-holding device 120, to sense a change of an internal air pressure of the pulse-holding device 120 caused by beats of the pulse. Operation of this type of the pulse-holding device 120 is known by those skilled in the art, and is not repeated herein. In another example, the sensing device 110 is a photoplethysmography (PPG) module including a light emitting diode (LED) and a photo detector (not shown). A change of a blood volume can be detected via a photoelectric means when beats of the pulse occur, so as to measure the blood pressure wave. The pulse-holding device 120 secures the PPG module to the position of the pulse, and provides an effect of resonance with the pulse.

The pulse diagnosis measurement device 100 further includes a processing device 130 for performing a signal processing on the pulse signal generated by the sensing device 110, such as a Fourier transform, to generate pulse diagnosis information. According to a theory of a Fourier analysis or the Fourier transform, any periodic wave in a time domain can be converted into harmonics (or harmonic components) in a frequency domain. Since the blood pressure wave can be regarded as a periodic wave, the processing device 130 can perform the Fourier transform on the pulse signal which is obtained by the sensing device 110 sensing the blood pressure wave, to generate harmonics of the blood pressure wave. The pulse diagnosis measuring device 100 is designed to obtain accurate information of specific harmonics by measuring the blood pressure wave. That is, the pulse diagnosis measuring device 100 can accurately measure one or some specific harmonics of the blood pressure waves. To accurately measure a specific harmonic, the pulse-holding device 120 should have specific physical conditions to resonate with the specific harmonic. Specifically, the pulse-holding device 120 (such a tourniquet) may oscillate (e.g., vibrate) with beats of the pulse, when measuring the blood pressure wave. Thus, the pulse-holding device 120 should have an appropriate elasticity coefficient to oscillate to fully match relaxation and contraction of the pulse. If the elasticity coefficient is too small or too large, the pulse-holding device 120 may be too soft or too hard, which results that no data is generated or damping is too high. As a result, an inaccurate measurement result is obtained. For example, a pulse diagnosis measurement device using a pressure sensor cannot measure variation of pressure accurately due to an inappropriate elasticity coefficient of the pulse diagnosis measurement device. A pulse diagnosis measurement device using a PPG technique cannot measure volume variation of light accurately caused by relaxation and contraction of a blood vessel due to an inappropriate elasticity coefficient of the pulse diagnosis measurement device. Furthermore, a harmonic of a higher frequency needs a larger elasticity coefficient to achieve a resonance, so as to obtain accurate harmonic information. Conversely, a harmonic of a lower frequency needs a smaller elasticity coefficient to achieve the resonance. In other words, an elasticity coefficient of the pulse-holding device 120 has a specific correspondence with a frequency of a harmonic to be measured. It can also be said that the elasticity coefficient of the pulse-holding device 120 is selected or determined according to the frequency of the harmonic to be measured. For example, the pulse-holding device 120 has a first elasticity coefficient corresponding to a first frequency of a first harmonic of the blood pressure wave. The processing device 130 can process a measured pulse signal (including its Fourier transform), to generate pulse diagnosis information of the first harmonic. The first harmonic may be a first integer harmonic or a first fractional harmonic. It should be noted that in the present specification, the first harmonic and the second harmonic are simply general terms for harmonics to distinguish with each other, and are not specifically referred to the first harmonic and the second harmonic in the signal analysis theory. In general, an amplitude of an integer harmonic of a blood pressure wave decreases as a frequency of the integer harmonic increases. Thus, it is difficult to measure an integer harmonic of a high frequency accurately. In addition, it is difficult to measure a fractional harmonic of a low frequency. Therefore, it is extremely important to determine elasticity coefficients of the pulse-holding device 120 for the harmonics difficult to be measured.

In one example, an elasticity coefficient of the pulse-holding device 120 is adjustable or switchable. For example, the pulse-holding device 120 can be switched to have a second elasticity coefficient different from the first elasticity coefficient. The second elasticity coefficient may be corresponding to a second frequency of a second harmonic of the blood pressure wave. The second harmonic may be a second integer harmonic or a second fractional harmonic.

The processing device 130 processes a measured pulse signal to generate pulse diagnosis information of the second harmonic. In other words, the elasticity coefficient of the pulse-holding device 120 can be adjusted in response to the frequency of the harmonic to be measured. Specifically, the second elasticity coefficient is greater than the first elasticity coefficient, when the second frequency of the second harmonic is greater than the first frequency of the first harmonic. It should be noted that a correspondence between an elasticity coefficient and a frequency of a harmonic may not be one-to-one, and an elasticity coefficient may be corresponding to a frequency band. In other words, the pulse-holding device 120 of a same elasticity coefficient can be suitable for measuring harmonics of a specific frequency band. Therefore, whether the elasticity coefficient of the pulse-holding device 120 needs to be adjusted depends on whether the frequency of the harmonic to be measured falls within the frequency band in which the elasticity coefficient is suitable for performing a measurement. In one example, the pulse-holding device 120 includes a plurality of tourniquets for adjusting or switching an elasticity coefficient. For example, the tourniquets can be used separately when the tourniquets have different elasticity coefficients, or several tourniquets can be connected in series or in parallel to produce different elasticity coefficients.

In one example, when the first harmonic is a first integer harmonic, the first frequency of the first harmonic is n times the fundamental frequency (i.e., heart rate) of the blood pressure wave, where n is an integer and $1 \leq n \leq 10$. In this example, the first elasticity coefficient is corresponding to a pressure-strain modulus Ep. When the fundamental frequency of the blood pressure wave is f Hz, $0.83 \leq f \leq 1.5$, the first elasticity coefficient is not smaller than $3.5*10^6$ dyn/cm$^2$, or the first elasticity coefficient is not smaller than $3.5*10^6$ dyn/cm$^2$ and not greater than $9.82*10^6$ dyn/cm$^2$.

In hemodynamics, the pressure-strain modulus Ep is used for representing an elasticity coefficient of a blood vessel, which is defined as $Ep=\Delta P*R_0/\Delta R_0$, where Ep is in a unit of dyn/cm$^2$, $R_0$ is a radius of the blood vessel, and $\Delta R_0$ is a length difference compared with $R_0$, and $\Delta P$ is the amount of change of a pressure. The above equation can be rewritten as $Ep=\Delta P/(\Delta R_0/R_0)$, and $\Delta R_0/R0$ is the length difference per unit radial length. Thus, Ep can be regarded as a radial elasticity coefficient of the blood vessel. Furthermore, $\Delta P$ is a pressure applied by harmonics and $\Delta R_0$ is a change of a radial length caused by the pressure, if the blood pressure wave is decomposed into the harmonics. In other words, each harmonic has its corresponding pressure-strain modulus Ep. Therefore, a better resonance with the blood vessel can be obtained, and a more accurate measurement result can be obtained, if the first elasticity coefficient of the pulse-holding device 120 can be matched to the pressure-strain modulus Ep of each harmonic. In other words, in this example, the first elasticity coefficient of the pulse-holding device 120 is used for measuring a relation between a radial stress and a radial strain. For example, the radial elasticity coefficient can be calculated, when the pulse-holding device 120 is a tourniquet which surrounds the pulse position (e.g., a wrist, an arm, a finger, etc.) to form a circle or an arc. A circle or an arc is formed when the pulse-holding device 120 is worn, if the pulse-holding device 120 is made into a wearable device such as a finger cot, a watch, a bracelet, a wristband, an armband, a foot ring, a headscarf or a collar, and a radial elasticity coefficient can be calculated. For another example, the portion of two ends of a clip contacting to an organism can be regarded as an arc, when the pulse-holding device 120 is the clip, and a radial elasticity coefficient can be also calculated. Thus, the numerical range of the first elasticity coefficient as mentioned above includes numerical values of a radial elasticity coefficient suitable for measuring a n-order integer harmonic ($1 \leq n \leq 10$).

In one example, when the first harmonic is a first fractional harmonic, the first frequency of the first harmonic is n times the fundamental frequency of the blood pressure wave, where n is a fraction and $0<n<1$. In this example, the first elasticity coefficient is corresponding to a pressure-strain modulus Ep. When the fundamental frequency of the blood pressure wave is f Hertz, $0.8 \leq f \leq 1.5$, the first elasticity coefficient is not smaller than $0.16*10^6$ dyn/cm$^2$ and is not greater than $3.5*10^6$ dyn/cm$^2$. This example shows that not only the integer harmonic but also the fractional harmonic of the lower frequency have their applicable range of radial elasticity coefficients.

Figure 2:
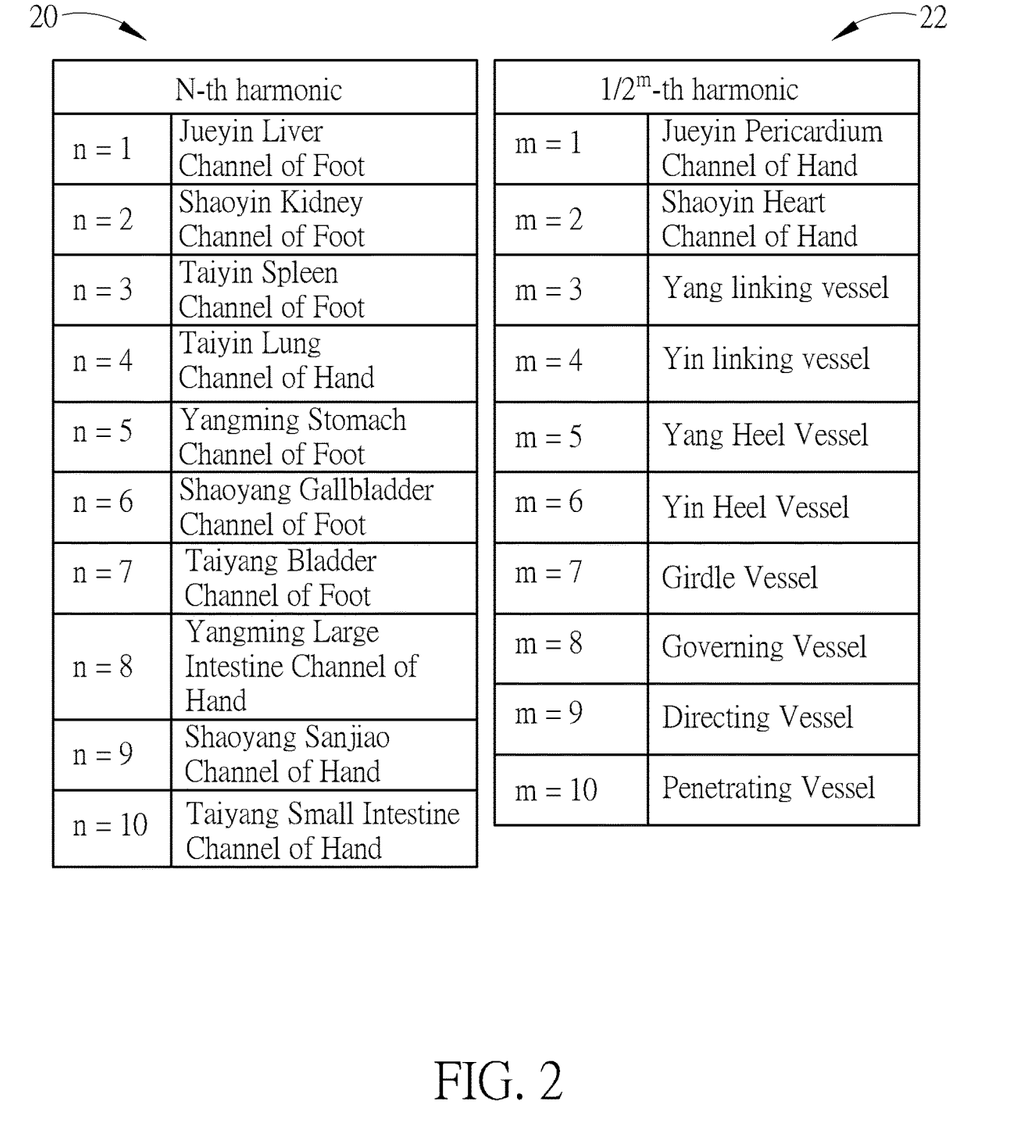
FIG. 2 is a correspondence table of harmonics of frequencies and human meridians according to an example of the present invention.
Figure 3:
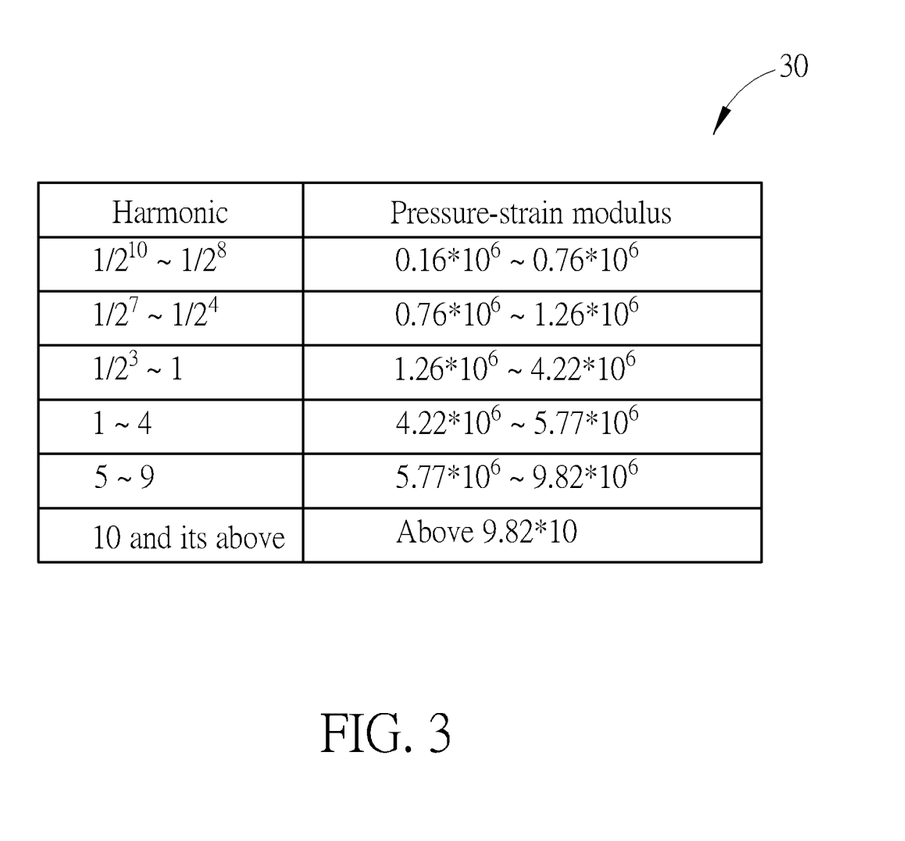
FIG. 3 is a correspondence table of frequencies of harmonics and pressure-strain modulus according to an example of the present invention.
Figure 4:
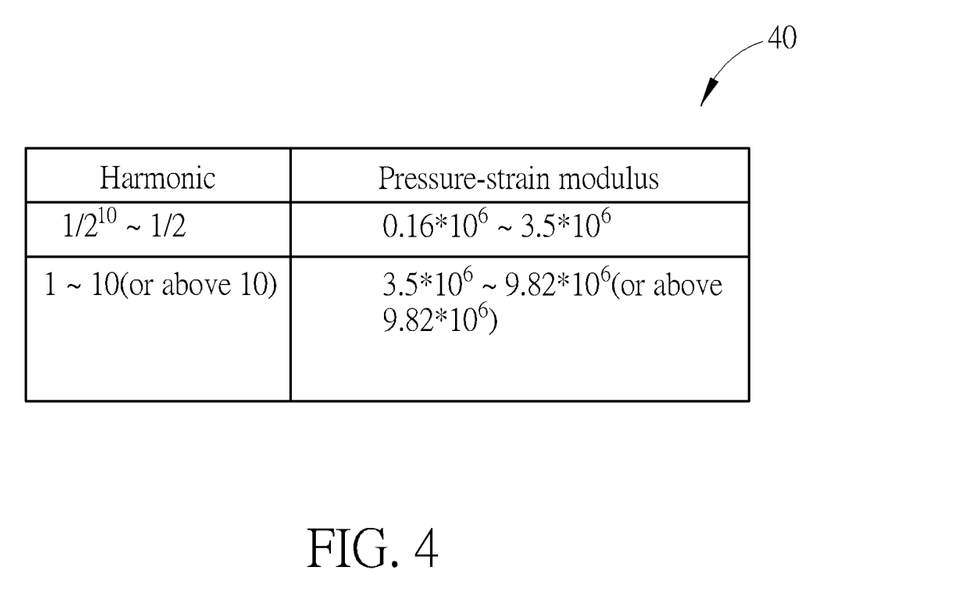
FIG. 4 is a correspondence table of frequencies of harmonics and pressure-strain modulus according to an example of the present invention.

In one example, the pulse diagnosis measurement device 100 is used for measuring the harmonic of the fundamental frequency of the blood pressure wave of the human body and harmonics of frequencies of n times the fundamental frequency (there are a total of 10 integer harmonics, where n=1, 2, 3, 4, 5, 6, 7, 8, 9, 10, and n=1 is the harmonic of the fundamental frequency) and 10 fractional harmonics of frequencies below the fundamental frequency (i.e., ½, ¼, ⅛, 1/16, 1/32, 1/64, 1/128, 1/256, 1/512, 1/1024 times of the fundamental frequency), which can be expressed as $½^m$-th harmonics, where m=1, 2, 3, 4, 5, 6, 7, 8, 9, 10. The twenty harmonics are corresponding to the twelve standard meridians and the eight extraordinary meridians, respectively, described in a theory of Chinese medicine, as shown in FIG. 2. FIG. 2 includes correspondence tables 20 and 22. The correspondence table 20 shows the meridians corresponding to the 10 integer harmonics above the fundamental frequency (inclusive). The correspondence table 22 shows the meridians corresponding to the $10½^m$-th harmonics. Each harmonic can display an energy state of a corresponding meridian, which has physiological significance and pathological significance. Thus, the pulse diagnosis measurement device 100 greatly helps the analysis and diagnosis of Chinese medicine by measuring these harmonics of the human body. FIG. 3 is a correspondence table 30 of the twenty harmonics and elasticity coefficients of the pulse-holding device 120, wherein a unit of the elasticity coefficient is dyn/cm$^2$. After determining a frequency range (i.e., frequency group of the harmonic) belonged to a frequency of a harmonic to be measured, the pulse-holding device 120 can be switched to a corresponding elasticity coefficient according to the correspondence table 30, to perform the measurement. Compared with a conventional measurement device where an elasticity coefficient needed for a tourniquet part is not considered, this method can improve the accuracy of the measurement. FIG. 4 is another correspondence table 40 of the twenty harmonics and elasticity coefficients of the pulse-holding device 120, wherein the unit of the elasticity coefficient is also dyn/cm$^2$. Compared with the correspondence table 30, the correspondence table 40 simplifies the number of groups of frequencies of harmonics, which simplifies a design of the pulse-holding device 120. It should be noted that the correspondence tables in FIG. 3 and FIG. 4 are only for exemplifying the present invention, and a scope of the present invention is not limited hereto.

In another example, since different organisms have different numbers of meridians, values of n and m described above may be adjusted according to the organism to be measured, to measure n integer harmonics and m fractional harmonics of the organism. As for elasticity coefficients of the pulse-holding device 120 corresponding to these harmonics, those skilled in the art can evaluate and select the elasticity coefficients by referring to the pressure-strain modulus Ep of the blood vessel of the organism, according to the examples of the present invention.

It should be noted that those skilled in the art are familiar with the fact that elasticity coefficients may change slightly due to various factors. Therefore, the scope of the present invention is not limited to the specific ranges of the above-mentioned elasticity coefficients, but includes an adjustment space. For example, the upper limit and the lower limit of the range of values may be adjusted from 10% to 20%. In addition, the range of the fundamental frequency of the blood pressure wave mentioned above may have an adjustment space according to actual situations. For example, the upper limit and the lower limit of the frequency range may allow an adjustment of 10% to 20%.

The present invention also provides a method of designing the pulse-holding device 120. According to the above description, in order to accurately measure the harmonics of different frequencies of the blood pressure wave, the pulse-holding device 120 needs to have matched resonance conditions, wherein the matched elasticity coefficient of the pulse-holding device 120 is the most critical one. One of main factors for determining the elasticity coefficient is a material used for the pulse-holding device 120, particularly a portion contacted to the organism (such as the pulse and its surrounding area). Thus, in one example, an appropriate pulse-holding material is determined based on a result of the Fourier analysis of the blood pressure wave. Specifically, the blood pressure wave is measured by using the pulse-holding device 120 made of a certain material, and amplitudes of harmonics of the blood pressure wave are obtained by using the Fourier analysis and are recorded. Then, the pulse-holding device 120 made of various materials (or mixed materials) repeats the processes described above, and performances of the materials when measuring the harmonics can be compared. For a specific harmonic, the larger the amplitude, the elasticity coefficient of the material is to cause the pulse-holding device 120 to generate a greater resonance with the harmonic, and thus the more suitable for measuring the harmonic. Thus, for a specific harmonic, a material capable of generating a maximum amplitude of the harmonic can be selected to make the pulse-holding device 120. In another example, a maximum area of the harmonic can be used for selecting the appropriate pulse-holding material. An area of a harmonic here refers to an area covered by a waveform of one or more periods of the harmonic. Thus, the maximum area of the harmonic is used as a reference standard. That is, in the measurement process, the maximum areas that can be generated by harmonics of different frequencies under different pulse-holding materials are compared to select a pulse-holding material that can generate the maximum area of the harmonic at a specific frequency/band.

In one example, if the blood pressure wave is measured by the pulse-holding device 120 being gently pressed on the arterial, a pulse-holding material is selected according to the maximum amplitude of the harmonic. In this situation, when a harmonic has the largest amplitude, the most suitable measurement state is achieved, and at this time the pressure of the pulse-holding device 120 is the diastolic blood pressure. In another example, if the blood pressure wave is measured by the pulse-holding device 120 of an inflatable type being pressed on the arterial, the pulse-holding material is selected according to the maximum area of the harmonic. In this situation, when a harmonic has the largest area, the most suitable measurement state is achieved, and at this time the pressure of the pulse-holding device 120 is the diastolic blood pressure.

In addition to the pulse-holding material described above, the factor of determining the elasticity coefficient of the pulse-holding device 120 may also include an external form of the pulse-holding device 120. For example, if the pulse-holding device 120 is a tourniquet, even with the same material, an elasticity coefficient of the tourniquet enclosing one circle is different from an elasticity coefficient of the tourniquet enclosing two circles (enclosing two circles is equivalent to connecting two tourniquets with the same material in parallel). For another example, an elasticity coefficient of the tourniquet made into a mesh is different from an elasticity coefficient of the tourniquet with a solid form with the same material. However, one of main features of the present invention, i.e., when designing a pulse-holding device, it is possible to generate a matched radial elasticity coefficient corresponding to a pressure-strain modulus of a blood vessel (which varies with frequencies of different harmonics). In other words, there should be a suitable correspondence between the frequency of a harmonic to be measured and the elasticity coefficient of the pulse-holding device. No matter which material or which external form is used by the pulse-holding device, if the correspondence is ignored, problems occur when measuring a certain harmonic such as an integer harmonic of a high frequency or a fractional harmonic of a low frequency. Thus, as long as those skilled in the art keep the main feature, a pulse-holding device with a matched elasticity coefficient can be designed according to practical applications, without being limited to the material and the external form described above. For example, for practical applications, due to different depths of pulses within the body, different measured parts of an organism may have different dampings. A pulse from a superficial part, such as a finger or a wrist, has a lower damping, while a pulse covered by thicker tissue of the organism, such as an arm, has a higher damping. Thus, when measuring a part with a higher damping, a lighter material can be selected to reduce the damping. In addition, due to a longer wavelength, a low-frequency harmonic is not easily affected by tissue of the organism. Thus a suitable measured part can be selected according to the frequency of a harmonic to be measured.

Figure 5:
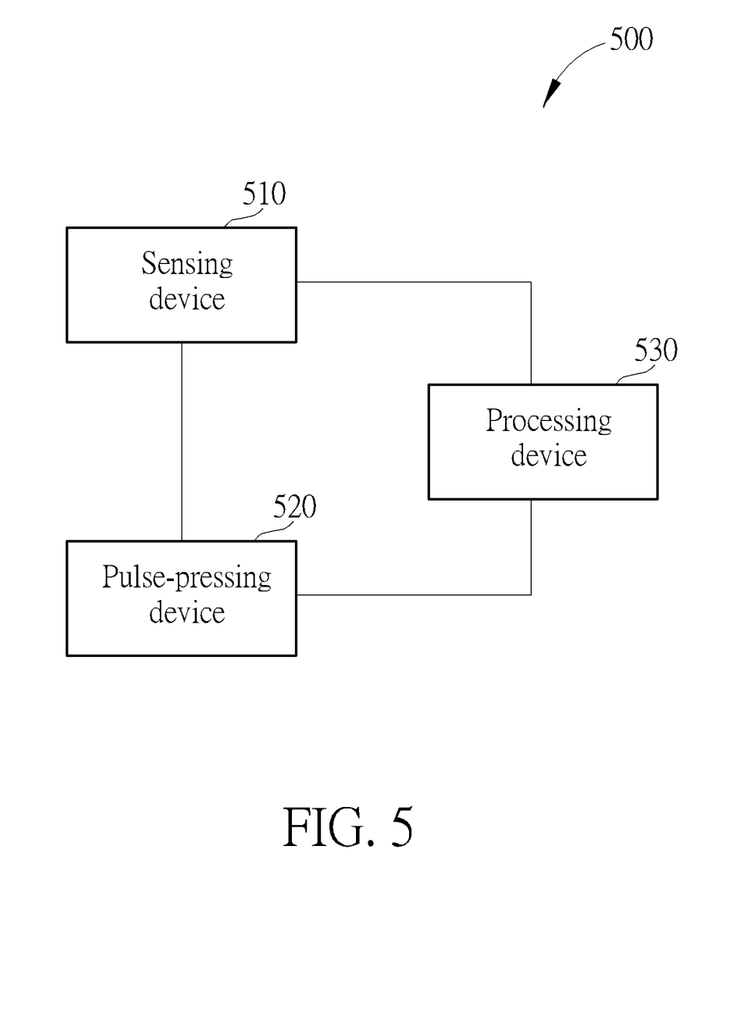
FIG. 5 is a schematic diagram of a pulse diagnosis measurement device according to an example of the present invention.

To accurately measure a blood pressure wave and its harmonics of different frequencies, a pulse-holding device may need to have suitable resonance conditions. In addition to the most critical matched elasticity coefficients described above, the resonance conditions also include a suitable pressure applied by the pulse-holding device to a pulse. The harmonics are difficult to be measured accurately, if one of the following situations happens: the pressure is too small to form a resonance, and the pressure is too large and is larger than a diastolic blood pressure. Thus, the present invention provides an example for another pulse diagnosis measurement device, which may dynamically adjust a pressure of the pulse-holding device to change a resonance condition during a measurement process, to match a blood pressure wave and its harmonics to be measured, so as to achieve a better measurement result. FIG. 5 is a schematic diagram of a pulse diagnosis measurement device according to an example of the present invention. In FIG. 5, a pulse diagnosis measurement device 500 may be a pulse diagnosis device, an electronic blood pressure monitor, a finger diagnosis device or other blood pressure wave measurement device. As shown in FIG. 5, the pulse diagnosis measurement device 500 includes a sensing device 510, for sensing a blood pressure wave of an organism, to generate a first pulse signal. The pulse diagnosis measurement device 500 further includes a pulse-holding device 520, for applying a pressure on a pulse of the organism. The pulse diagnosis measurement device 500 further includes a processing device 530, for computing a pulse pressure according to the first pulse signal, and continuing adjusting the pressure of the pulse-holding device 520 until the pulse pressure is not increased, at which time the pressure of the pulse-holding device 520 has a most suitable pressure value. The processing device 530 further senses the blood pressure wave according to the most suitable pressure value, to generate a second pulse signal. There are various ways to dynamically adjust the pressure of the pulse-holding device 520. For example, the pulse-holding device 520 may include an air bag, and the pressure of the pulse-holding device 520 may be adjusted by controlling the amount of air inflated into the air bag.

In the above examples, a magnitude of the pulse pressure is used for determining a suitable measurement state. The pulse pressure may be defined as a difference between a systolic blood pressure and a diastolic blood pressure. During the measurement process, the processing device 530 continuously increases the pressure of the pulse-holding device 520, and detects a maximum value and a minimum value of each blood pressure wave of the first pulse signal measured by the sensor device 510. Then, the processing device 530 subtracts the maximum value and the minimum value to obtain the pulse pressure. When the pressure of the pulse-holding device 520 is increased and the pulse pressure is not increased, a suitable measurement state is achieved. Thus, a pressure value applied by the pulse-holding device 520 to the maximum pulse pressure is the suitable pressure value, which represents a suitable resonance condition of the blood pressure wave, such that the pulse diagnosis measurement device 500 achieves the suitable measurement state. At this time, pulse diagnosis information of the second pulse signal generated is more accurate than that of the first pulse signal generated before the suitable measurement state is achieved. Thus, in one example, the processing device 530 further generates pulse diagnosis information of the organism according to the second pulse signal, wherein the pulse diagnosis information includes at least one of following information: a heart rate, a systolic blood pressure, a diastolic pressure and at least one harmonic of the blood pressure wave. For example, the most suitable pressure value described above is the diastolic blood pressure, and at that time, the systolic blood pressure is a sum of the diastolic blood pressure and the pulse pressure.

In the prior art, when measuring the blood pressure wave, a pressure of the tourniquet is continuously increased until the pressure is greater than a systolic blood pressure to block a blood flow of an arterial, and the pressure of the tourniquet is decreased until a Korotkoff sound (corresponding samples of the Korotkoff sound in an electronic blood pressure monitor) exists, such that the systolic blood pressure and a diastolic blood pressure can be obtained. Not only more time is needed for completing the measurement, but also the accuracy of the measurement is reduced due to that the blood flow of the arterial is blocked and the arterial is affected. In comparison, according to the examples in the present invention, not only less time is needed for completing the measurement, but also an influence on the arterial is reduced. Thus, the blood pressure wave and its harmonics are measured accurately, which facilitates further analysis.

Furthermore, in order to get a more accurate measurement result, pressure values of the pulse-holding device 120 needed for harmonics of different frequencies are slightly different. In general, a high frequency harmonic needs a higher pressure value, and a low frequency harmonic needs a lower pressure value. In one example, when the processing device 530 senses the blood pressure wave according to the optimal pressure value, the pressure of the pulse-holding device 520 is further adjusted according to a fine-tuned value to measure a specific harmonic (e.g., a fractional harmonic) of the blood pressure wave. The fine-tuned value is corresponding to a frequency of the specific harmonic. For example, when the frequency of the harmonic is lower than the fundamental frequency of the blood pressure wave, the pressure of the pulse-holding device 520 is reduced according to the fine-tuned value to measure the harmonic. For example, when the frequency of the harmonic is higher than the fundamental frequency of the blood pressure wave, the pressure of the pulse-holding device 520 is increased in according to the fine-tuned value to measure the harmonic. After the pressure of the pulse-holding device 520 is finely adjusted, the resonance of the pulse-holding device 520 with the harmonic is improved and a better measurement result is obtained. For example, when performing a Fourier transform on the measured blood pressure wave, it is observed that an amplitude of a specific harmonic becomes larger or an area covered by a waveform of at least one cycle of the specific harmonic becomes larger. In one example, the abovementioned fine-tuned value may be determined or dynamically adjusted according to a result of the Fourier analysis on the blood pressure wave. For example, the fine-tuned value may be selected (or dynamically adjusted to) such that the amplitude of the specific harmonic or the area covered by the waveform of the specific harmonic becomes larger. Specifically, the amplitude of the specific harmonic H can be obtained from the result of the Fourier analysis on the blood pressure wave. By slightly increasing or decreasing the pressure of the pulse-holding device 520, a measurement state is the most appropriate measurement state when the amplitude of the harmonic H is maximized. At this time, the pressure of the pulse-holding device 520 has the most suitable pressure value for measuring the harmonic H. Comparing this pressure value with the abovementioned most suitable pressure value, the fine-tuned value corresponding to the harmonic H can be obtained. The above method of determining the fine-tuned value according to the maximum amplitude of the harmonic may also be performed according to the maximum area of the harmonic (i.e., the area covered by the waveform of the at least one period is maximized).

Figure 6:
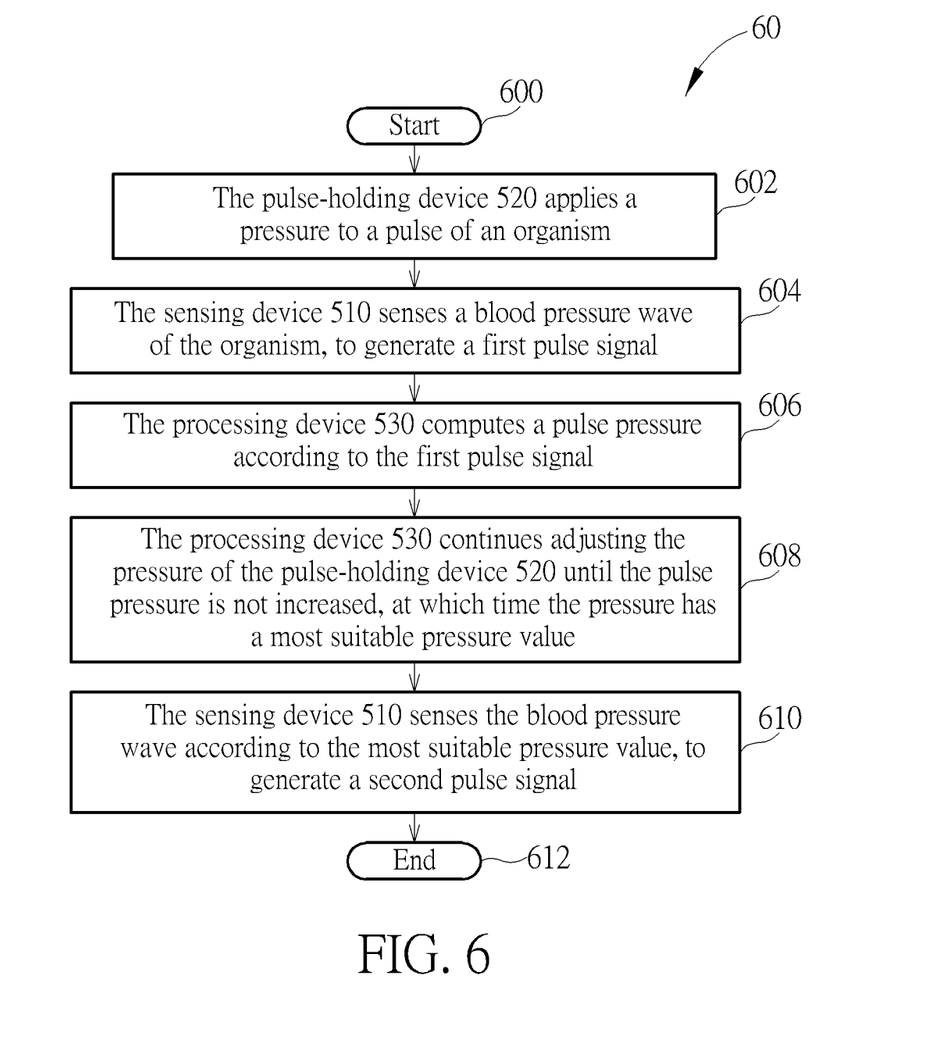
FIG. 6 is a flowchart of a pulse diagnosis measurement method according to an example of the present invention.

The above examples can be summarized as FIG. 6, which is a flowchart of a process 60 according to the examples of the present invention. The process 60 states a pulse diagnosis measurement method performed by the pulse diagnosis measurement device 500, and includes the following steps:

Step 600: Start.

Step 602: The pulse-holding device 520 applies a pressure to a pulse of an organism.

Step 604: The sensing device 510 senses a blood pressure wave of the organism, to generate a first pulse signal.

Step 606: The processing device 530 computes a pulse pressure according to the first pulse signal.

Step 608: The processing device 530 continues adjusting the pressure of the pulse-holding device 520 until the pulse pressure is not increased, at which time the pressure has a most suitable pressure value.

Step 610: The sensing device 510 senses the blood pressure wave according to the most suitable pressure value, to generate a second pulse signal.

Step 612: End.

The present invention further provides a pulse diagnosis analysis method, which can be applied to the pulse diagnosis measurement device 100 and the pulse diagnosis measurement device 500, or other pulse diagnosis devices such as a pulse instrument, an electronic blood pressure monitor, a finger diagnosis device, other blood wave measurement devices, etc. If the method is applied to the pulse diagnosis measurement device 100 (or the pulse diagnosis measurement device 500), a measurement of a blood pressure wave is performed by the sensing device 110 (or the sensing device 510) and the pulse-holding device 120 (or the pulse-holding device 520). The processing device 130 (or the processing device 530) performs subsequent data analysis and processing according to the measurement result. In one example of the pulse diagnosis analysis method, a heart rate HR is obtained according to a wave length (e.g., the number of covered samples) of the blood pressure wave which is measured stably and well for t seconds (a preferred value of t is 6) and a sampling rate. Then, a Fourier analysis is performed on the blood pressure wave, and harmonic amplitudes An and harmonic phase differences en of 10 integer harmonics (fn, n=1, 2, 3, 4, 5, 6, 7, 8, 9, 10) above a fundamental frequency fl (inclusive) are obtained. In one example, "a stable and good measurement" means that a premature contraction of a heart is filtered out from the blood pressure wave.

Then, the heart rate HR, the harmonic amplitudes An and the harmonic phase differences en are averaged respectively to obtain means and standard deviations (SDs). The SDs are divided by the averages to obtain variation coefficients which include a heart rate variation coefficient HRCV and variation coefficients of the harmonic amplitudes HCVn and variation coefficients of the harmonic phase differences HPCVn. The HCVn and the HPCVn are divided respectively by the HRCV, to obtain failure indices of the harmonic amplitudes and the harmonic phase differences. Failure indices of the harmonic amplitudes FIAn represent pathological conditions of a gas phase, and failure indices of the harmonic phase differences FIPn represent pathological conditions of a blood phase. Higher values of the failure indices FIAn and FIPn mean more dangerous conditions of a measured organism (e.g., patient). If the values of the failure indices FIAn and FIPn are reduced by using a handling or a treatment on the organism, it means that the handling or the treatment is effective.

For ease of understanding, calculation of the above parameters is organized as follows. The failure indices FIAn of the harmonic amplitudes An and the failure indices FIPn of the harmonic phase differences θn are expressed as follows:

$$FIAn = HCVn/HRCV, \text{ where } n=1,2,3,4,5,6,7,8,9,10; \quad (Eq.\ 1)$$

$$FIPn = HPCVn/HRCV, \text{ where } n=1,2,3,4,5,6,7,8,9,10. \quad (Eq.\ 2)$$

Some parameters regarding the mean of a heart rate HRM and the standard deviation of the heart rate HRV are expressed as follows:

$$HRCV = HRV/HRM; \quad (Eq.\ 3)$$

$$HRVM = HRV*HRM. \quad (Eq.\ 4)$$

Variation coefficients of the harmonic amplitudes HCVn and variation coefficients of the harmonic phase differences HPCVn are expressed as follows:

$$HCVn = \text{Standard Deviation of } n\text{-th harmonic amplitude/Mean of } n\text{-th harmonic amplitude, where } n=1,2,3,4,5,6,7,8,9,10; \quad (Eq.\ 5)$$

$$HPCVn = \text{Standard Deviation of } n\text{-th harmonic phase difference/Mean of } n\text{-th harmonic phase difference, where } n=1,2,3,4,5,6,7,8,9,10. \quad (Eq.\ 6)$$

Regarding the above parameters, the HRCV and the HRVM in the equations (Eq. 3) and (Eq. 4) are related to a brain death. The fundamental frequency (n=1) and the 4-th harmonic (n=4) are related to a heart failure. Thus, the failure indices of the harmonic amplitudes of the fundamental frequency and the 4-th harmonic (i.e., HCV1 and HCV4) and the failure indices of the harmonic phase differences of the fundamental frequency and the 4-th harmonic (i.e., HPCV1 and HPCV4) can be used for assisting the diagnosis and the treatment.

In one example, according to the abovementioned parameters, a pathological matrix is defined as follows:

$$[\text{Mean}[An]/P\text{Mean}[\theta n]HCVn\ HPCVn\ FIAn\ FIPn], \quad (Eq.\ 7)$$

where n=1, 2, 3, 4, 5, 6, 7, 8, 9, 10. Mean[An] and Mean[θn] are average values of the harmonic amplitudes An and the harmonic phase differences θn, respectively. P is energy of entrails (five organs are a heart, a liver, kidney(s), a spleen and lung(s), and six organs are a stomach, a gall bladder, a large intestine, a small intestine, a urinary bladder and a triple energizer), and is defined as follows:

$$P = \Sigma_{i=1}^{10} Ai. \quad (Eq.\ 8)$$

Then, in a time interval T (e.g., within that a blood pressure is measured), a Fourier analysis is performed on a plurality of blood pressure wave sequences measured in each t consecutive seconds (a preferred value of t is 6). Accordingly, harmonic amplitudes $A(\frac{1}{2}'')$ and harmonic phase differences $\theta(\frac{1}{2}'')$ of 10 fractional harmonics $f(\frac{1}{2}'')$ (n=1, 2, 3, 4, 5, 6, 7, 8, 9, 10) below the fundamental frequency f1 are obtained. The heart rate HR, the harmonic amplitudes $A(\frac{1}{2}'')$ and the harmonic phase differences $\theta(\frac{1}{2}'')$ are averaged respectively to obtain means and a deviation. The deviation is divided by the means to obtain variation coefficients which include a heart rate variation coefficient HRCV and variation coefficients of harmonic amplitudes $HCV(\frac{1}{2}'')$ and variation coefficient of harmonic phase differences $HPCV(\frac{1}{2}'')$. The $HCV(\frac{1}{2}'')$ and the $HPCV(\frac{1}{2}'')$ are divided respectively by the HRCV, to obtain failure indices of the harmonic amplitudes and the harmonic phase differences. Failure indices of the harmonic amplitudes $FIA(\frac{1}{2}'')$ represent pathological conditions of a gas phase, and failure indices of the harmonic phase differences $FIP(\frac{1}{2}'')$ represent pathological conditions of a blood phase. Higher values of the failure indices $FIA(\frac{1}{2}'')$ and $FIP(\frac{1}{2}'')$ mean more dangerous conditions of a measured organism (e.g., patient). If the values of the failure indices $FIA(\frac{1}{2}'')$ and $FIP(\frac{1}{2}'')$ are reduced by using a handling or a treatment on the organism, it means that the handling or the treatment is effective.

In one example, according to the abovementioned parameters, a low-frequency pathological matrix is defined as follows:

$$[\text{Mean}[A(\tfrac{1}{2}'')]/Q\text{Mean}[\theta(\tfrac{1}{2}'')]HCV(\tfrac{1}{2}'')HPCV(\tfrac{1}{2}'')\ FIA(\tfrac{1}{2}'')FIP(\tfrac{1}{2}'')], \quad (Eq.\ 9)$$

where n=1, 2, 3, 4, 5, 6, 7, 8, 9, 10. Mean $[A(\frac{1}{2}'')]$ and Mean $[\theta(\frac{1}{2}'')]$ are average values of the harmonic amplitudes $A(\frac{1}{2}'')$ and the harmonic phase differences $\theta(\frac{1}{2}'')$, respectively. Q is energy of a heart and an aorta, and is defined as follows:

$$Q = \Sigma_{i=1}^{10} A(\tfrac{1}{2}^i). \quad (Eq.\ 10)$$

Figure 7:
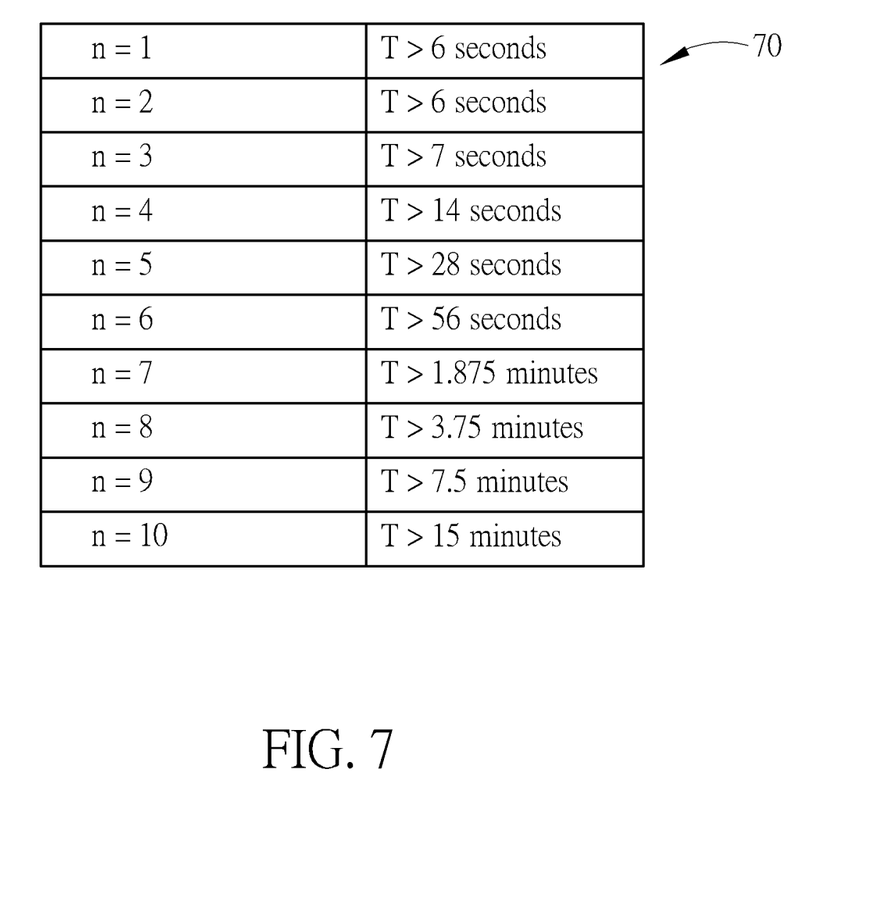
FIG. 7 is a correspondence table of frequencies of harmonics $f(\frac{1}{2}'')$ and a time interval T according to an example of the present invention.

Then, in a time interval T (e.g., within that a blood pressure is measured), low-frequency pathological matrices in each t consecutive seconds (a preferred value of t is 6) are averaged, and an averaged low-frequency pathological matrix Mean [Low f Pathological Matrix] is obtained. The time interval T may be determined according to a frequency of a harmonic (i.e., varies with n). For example, when n is larger, the time interval T needed is larger. FIG. 7 is a correspondence table of frequencies of harmonics $f(\frac{1}{2}'')$ and the time interval T according to an example of the present invention. The correspondence table 70 illustrates the time interval T corresponding to each harmonic frequency $f(\frac{1}{2}'')$.

The pathological matrix and the low-frequency pathological matric can be combined to analyze basic conditions and variations of physiology, pathology, pharmacology and psychology of an organism. The above examples may be analyzed via artificial intelligence, and are served as a basis of a human interface platform.

In one example, two parameters related to a pulse diagnosis are defined as follows:

$$R = \Sigma_{i=8}^{10} A(\tfrac{1}{2}^i), \text{energy of a heart and an aorta;} \quad (Eq.\ 11)$$

$$S = A(\tfrac{1}{2}^{10}), \text{energy of the heart.} \quad (Eq.\ 12)$$

Figure 8:
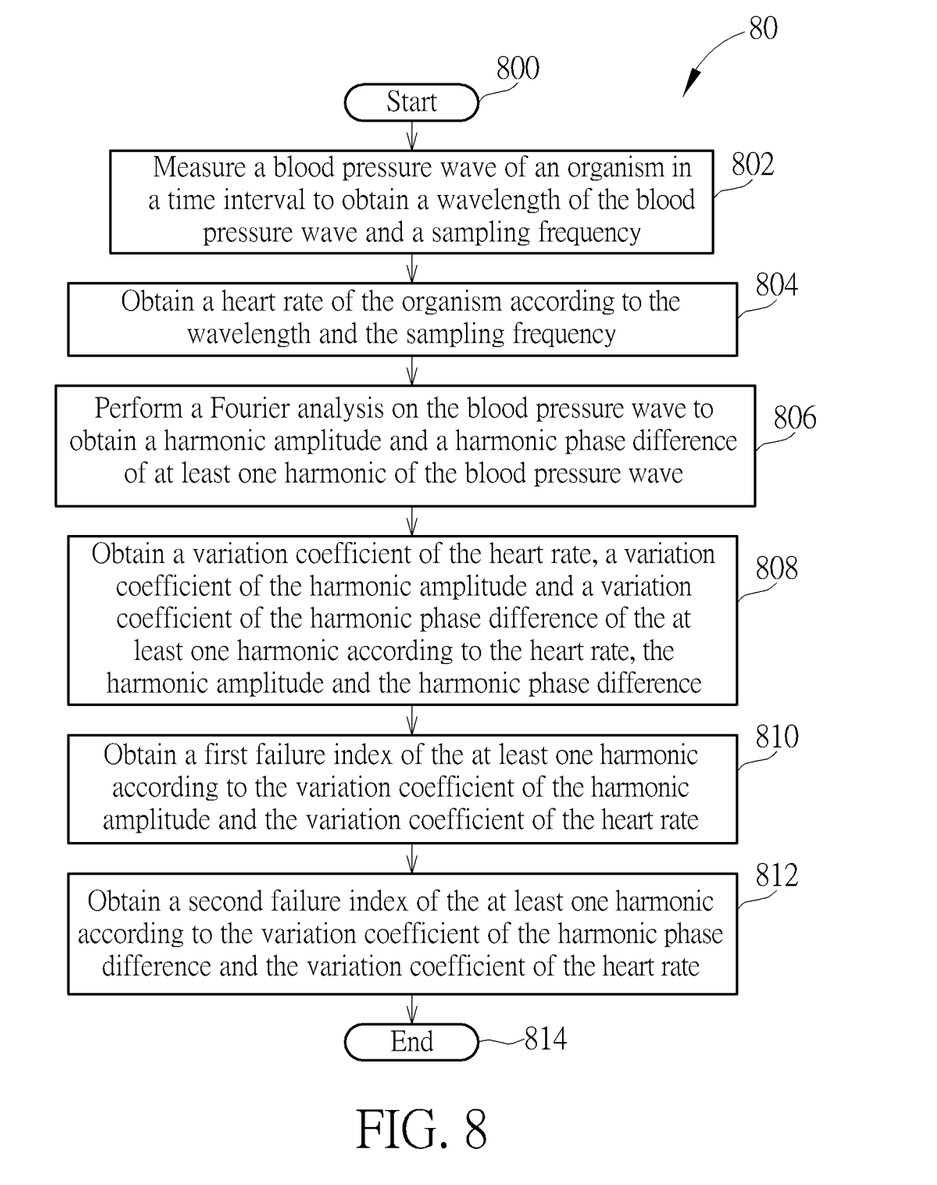
FIG. 8 is a flowchart of a pulse diagnosis analysis method according to an example of the present invention.

The above examples can be summarized as FIG. 8, which is a flowchart of a process 80 according to the examples of the present invention. The process 80 states a pulse diagnosis measurement method, and includes the following steps:

Step 800: Start.

Step 802: Measure a blood pressure wave of an organism in a time interval to obtain a wavelength of the blood pressure wave and a sampling frequency.

Step 804: Obtain a heart rate of the organism according to the wavelength and the sampling frequency.

Step 806: Perform a Fourier analysis on the blood pressure wave to obtain a harmonic amplitude and a harmonic phase difference of at least one harmonic of the blood pressure wave.

Step 808: Obtain a variation coefficient of the heart rate, a variation coefficient of the harmonic amplitude and a variation coefficient of the harmonic phase difference of the at least one harmonic according to the heart rate, the harmonic amplitude and the harmonic phase difference.

Step 810: Obtain a first failure index of the at least one harmonic according to the variation coefficient of the harmonic amplitude and the variation coefficient of the heart rate.

Step 812: Obtain a second failure index of the at least one harmonic according to the variation coefficient of the harmonic phase difference and the variation coefficient of the heart rate.

Step 814: End.

There are various applications for the pulse diagnosis measurement device, the pulse diagnosis measurement method and the pulse diagnosis analysis method of the present invention. For example, a medical cloud may be realized accordingly. In detail, the pulse diagnosis measurement device 100 or the pulse diagnosis measurement device 500 may be used at a user end to obtain pulse diagnosis data of a patient. The pulse diagnosis data is uploaded to the medical cloud, and is analyzed and diagnosed according to the pulse diagnosis analysis method in the present invention. Then, prescription is generated according to results of the analysis and the diagnosis, and is provided to the user end to complete the medical procedure. The results of the analysis and the diagnosis and the prescription may be provided jointly, or only the prescription is provided. In one example, the present invention can be applied to condition monitoring. For example, a condition monitoring system (including, e.g., the pulse diagnosis measurement device 100 or the pulse diagnosis measurement device 500) is designed to generate pulse diagnosis data of a patient, to perform a condition monitoring. An alert is issued when abnormal data are detected, e.g., a variation coefficient or a failure index of a specific harmonic is abnormal.

Those skilled in the art should readily make combinations, modifications and/or alterations on the abovementioned description and examples. The abovementioned description, steps and/or processes including suggested steps can be realized by means that could be hardware, software, firmware (known as a combination of a hardware device and computer instructions and data that reside as read-only software on the hardware device), an electronic system, or combination thereof.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A pulse diagnosis measurement system, comprising:
   a sensor configured to sense a blood pressure wave of an organism, to generate a pulse signal;
   a pulse-holding device, configured to apply a pressure on an artery of the organism to facilitate the sensor to sense the blood pressure wave; and
   a processing device, configured to generate pulse diagnosis information according to the pulse signal;
   wherein the pulse-holding device has an elasticity coefficient, the elasticity coefficient of the pulse-holding device is configured to be adjusted to a first elasticity coefficient when the sensor measures a first harmonic of the blood pressure wave having a first frequency with the sensor, the first harmonic is a first integer harmonic or a first fractional harmonic, the elasticity coefficient of the pulse-holding device is configured to be adjusted to a second elasticity coefficient greater than the first elasticity coefficient when the sensor measures a second harmonic of the blood pressure wave having a second frequency greater than the first frequency, the second harmonic is a second integer harmonic or a second fractional harmonic;
   wherein the pulse-holding device comprises a plurality of tourniquets;
   wherein the elasticity coefficient of the of the pulse-holding device is configured to be adjusted by using the plurality of tourniquets separately when the plurality of tourniquets have different elasticity coefficients, or by connecting the plurality of tourniquets in series or in parallel.

2. The pulse diagnosis measurement system of claim 1, wherein the first elasticity coefficient is a radial elasticity coefficient corresponding to a pressure-strain modulus of a blood vessel of the organism.

3. The pulse diagnosis measurement system of claim 2, wherein the first frequency of the first harmonic is n times a fundamental frequency of the blood pressure wave, the second frequency of the second harmonic is m times the fundamental frequency of the blood pressure wave, and n and m are integers where $1 \leq n < m \leq 10$, when the first harmonic is the first integer harmonic and the second harmonic is the second integer harmonic.

4. The pulse diagnosis measurement system of claim 2, wherein the first frequency of the first harmonic is n times a fundamental frequency of the blood pressure wave, the second frequency of the second harmonic is m times the fundamental frequency of the blood pressure wave, and n and m are fractions where $0 < n < m < 1$, when the first harmonic is the first fractional harmonic and the second harmonic is the second fractional harmonic.

5. The pulse diagnosis measurement system of claim 1, wherein the sensor is a pressure sensor.

6. The pulse diagnosis measurement system of claim 1, wherein the sensor is a photoplethysmography (PPG) module including a light emitting diode (LED) and a photo detector.

7. The pulse diagnosis measurement system of claim 3, wherein the first elasticity coefficient and the second elasticity coefficient greater than the first elasticity coefficient are not smaller than $3.5*10^6$ dyn/cm$^2$ and not greater than $9.82*10^6$ dyn/cm$^2$ when the fundamental frequency of the blood pressure wave is not less than 0.8 Hz and not greater than 1.5 Hz.

8. The pulse diagnosis measurement system of claim 4, wherein the first elasticity coefficient and the second elasticity coefficient greater than the first elasticity coefficient are not smaller than $0.16*10^6$ dyn/cm$^2$ and not greater than $3.5*10^6$ dyn/cm$^2$ when the fundamental frequency of the blood pressure wave is not less than 0.8 Hz and not greater than 1.5 Hz.

* * * * *